United States Patent [19]

Pommer et al.

[11] 4,143,153

[45] Mar. 6, 1979

[54] FUNGICIDE FOR WOOD PRESERVATION EMPLOYING COMPLEXED HEAVY METAL SALTS OF N-NITROSO-N-CYCLOHEXYLHYDROXYLAMINE

[75] Inventors: Ernst-Heinrich Pommer, Limburgerhof; Wolfgang Reuther, Ziegelhausen; Paul Raff, Ludwigshafen; Reimer Goettsche, Baden-Baden, all of Fed. Rep. of Germany

[73] Assignee: BASF Aktiengesellschaft, Ludwigshafen, Fed. Rep. of Germany

[21] Appl. No.: 551,907

[22] Filed: Feb. 21, 1975

[30] Foreign Application Priority Data

Mar. 6, 1974 [DE] Fed. Rep. of Germany ....... 2410603

[51] Int. Cl.$^2$ ............................................. A01N 9/00
[52] U.S. Cl. ................................... 424/289; 424/166; 424/167; 424/287; 424/294; 424/295; 424/325
[58] Field of Search ............... 424/167, 325, 287, 289, 424/294, 295, 166

[56] References Cited

U.S. PATENT DOCUMENTS

| 3,464,782 | 9/1969 | Ricard et al. | 424/325 |
| 3,629,466 | 12/1971 | Sander et al. | 424/325 |
| 3,755,595 | 8/1973 | Goring et al. | 424/325 |

*Primary Examiner*—V. D. Turner
*Attorney, Agent, or Firm*—Keil & Witherspoon

[57] ABSTRACT

A fungicidal composition for wood preservation containing derivatives of heavy metal salts of N-nitroso-N-cyclohexylhydroxylamine, and a process for combatting fungi with these derivatives.

10 Claims, No Drawings

FUNGICIDE FOR WOOD PRESERVATION EMPLOYING COMPLEXED HEAVY METAL SALTS OF N-NITROSO-N-CYCLOHEXYLHYDROXYLAMINE

The present invention relates to a fungicide for wood preservation containing derivatives of heavy metal salts of N-nitroso-N-cyclohexylhydroxylamine.

Wood must often be protected against attack by animal or fungous pests as they can destroy timber in a short period of time.

It is known to protect wood against fungus attack by treating it with numerous organic or inorganic compounds. However, many of these compounds are removed with the passage of time from the wood by leaching or as a result of volatilization.

It is known that N-nitroso-N-cyclohexylhydroxylamine (NCH) and its salts have a good fungicidal action. As the alkali metal salts of NCH are, relatively, easily soluble in water there is the danger that these salts will be leached out of the timber upon exposure to the elements. The heavy metal salts of NCH have extremely sparing solubility in water and cannot therefore be used in the form of aqueous solutions for wood preservation.

It is also known (German Laid-Open Application DOS No. 1,817,571) to use a composition of alkali metal hydroxide and a heavy metal salt, e.g., the zinc salt, of NCH as fungicide. However, the depth of penetration of this fungicide into the wood is poor.

We have now found that a fungicide does not have the abovementioned drawbacks when it contains a complex of a heavy metal salt, especially a copper, zinc, cadmium, nickel or cobalt salt, of NCH and an amine compound, particularly ammonia, a primary or secondary amine, a tertiary amine or an organic or inorganic compound containing an amine function in the molecule. The complex may be prepared by reacting a heavy metal salt of NCH with ammonia, an amine or a compound having an amine function. It may also be prepared by adding alkali metal or amine salts of NCH to the appropriate water-soluble heavy metal amine complex salts. The complexes of heavy metal salts of NCH with amino group-containing compounds are very readily soluble in aqueous media.

Treatment of the wood with the fungicides according to the invention may be carried out by impregnating, coating or painting it, with or without the application of pressure, with an aqueous solution of the fungicide, followed by drying. During drying, the action of the natural carbon dioxide in the air and that of the natural acid of the wood yield the sparingly soluble heavy metal salts from the soluble heavy metal amine salts of NCH, thus providing lasting protection against fungus attack. The impregnated wood may also be treated direct with carbon dioxide or other organic or inorganic acids, e.g., dilute sulfuric or acetic acid, instead of natural carbon dioxide.

Application rates are from 0.5 to 10 kg of active ingredient per $m^3$ of wood, and the concentration of active ingredient in the solutions is from 0.1 to 10, and preferably from 1 to 2, % (by weight). Wetting agents may be added if desired.

The fungicides of the invention are particularly effective on ligniperdous and soft rot fungi.

For complexing the heavy metal salts, especially the copper, zinc, cadmium, nickel and cobalt salts, of NCH almost all amine-containing compounds are suitable, e.g., ammonia, methylamine, ethylamine, propylamine, dimethylamine, triethylamine, higher secondary and tertiary amines, ethylenimine, ethylenediamine, propylenediamine, hexamethylenediamine, diethylenetetramine, tetraethylenepentamine, diethylenetriamine, dipropylenetriamine, tripropylenetetramine, and polyamines having primary, secondary and tertiary amine groups. Also suitable for complexing are organic and inorganic compounds containing in addition to the amine function other functional groups, e.g., hydroxyl, urea, carboxyl and phenol groups, for instance ethanolamine, aminocarboxylic acids, phenol-formaldehyde condensates containing amino groups, heterocycles with basic amine groups, e.g., 2-oxo-5-alkylhexahydro-1,3,5-triazines, imidazoles, pyrimidines, etc. Inorganic compounds with amino groups, e.g., hydroxylamine and hydrazine, are also suitable for converting the heavy metal salts of NCH into water-soluble complex salts.

Wood preservatives and wood preservative solutions of water-soluble heavy metal salts of NCH may for instance have the following compositions:

EXAMPLE 1

| | |
|---|---|
| 56.0% (by weight) of the potassium salt of NCH | |
| 44.0% of copper di-(ethylenediamine)-sulfate | |
| 100.0% | |

EXAMPLE 2

| | |
|---|---|
| 38.0% of the cyclohexylamine salt of NCH | |
| 62.0% of copper di-(ethylenediamino)-nitrate | |
| 100.0% | |

EXAMPLE 3

| | |
|---|---|
| 53.0% of the sodium salt of NCH | |
| 47.0% of copper di-(propylenediamino)-sulfate | |
| 100.0% | |

The concentration of the aqueous solution for Examples 1 to 3 for full impregnation by the vacuum method is from 1 to 2% (by weight) of the wood preservatives; for coating or spraying the concentration should be increased to about 3 to 7, and particularly, 5%.

EXAMPLE 4

Preparation of a wood preservative solution

| | |
|---|---|
| 1.2 parts (by weight) of a solution consisting of | |
| 33% $ZnSO_4 \cdot 7 H_2O$ | |
| 20% diethylenetetramine | |
| 47% $H_2O$ | | is added to 100 parts of a 0.6% solution of the potassium salt of NCH in water.

EXAMPLE 5

| | |
|---|---|
| 1.2 parts of a solution consisting of | |
| 33 parts of copper sulfate. 5 $H_2O$ | |
| 25 parts of tetraethylenepentamine | |
| 62 parts of $H_2O$ | | is added to 100 parts of a 0.6% solution of the sodium salt of NCH in water.

EXAMPLE 6

1.2 parts of a solution consisting of
33% of cadmium sulfate. 8 H$_2$O
20% of diethylenetriamine
47% of H$_2$O is added to 100 parts of a 0.6% solution of the potassium salt of NCH in water.

EXAMPLE 7

1.0 part of a solution consisting of
46% of nickel sulfate. 7 H$_2$O
20% of ethylenediamine
34% of water is added to 100 parts of a 0.6% solution of the potassium salt of NCH in water.

EXAMPLE 8

1.3 parts of a solution consisting of
35% of cobalt nitrate. 6 H$_2$O
18% of propylenediamine
47% of H$_2$O is added to 100 parts of a 0.6% solution of the sodium salt of NCH in water.

EXAMPLE 9

1.5 parts of a solution consisting of
25% of copper sulfate. 5 H$_2$O
25% of H$_3$BO$_3$
21% of dipropylenetriamine
29% of H$_2$O is added to 100 parts of a 0.6% solution of the potassium salt of NCH in water.

EXAMPLE 10

1.5 parts of a solution consisting of
25% of zinc sulfate. 7 H$_2$O
25% of boric acid
21% of diethylenetriamine
29% of H$_2$O is added to 100 parts of a 0.5% solution of the sodium salt of NCH in water.

By adding known diffusible wood preservatives, e.g., boron compounds, it is possible, after fixation in the wood of the salts of NCH, for diffusion to take place in the presence of moisture to inner non-impregnated areas, thus providing additional protection.

The solutions of the water-soluble heavy metal amine complexes, especially the copper and zinc amine complexes, of NCH may also be prepared for instance in the following manner. The heavy metal salts of NCH are dissolved in a stirred apparatus in the presence or absence of water in the minimum amount of the amine necessary for complexing.

EXAMPLE 11

600 parts of imidazole is added to 100 parts of the copper salt of NCH; the mixture is then heated, with stirring, to 50° C. After a short time the complex salt forms. The mixture is subsequently made up to 5,000 parts with water.

EXAMPLE 12

Wood preservative consisting of:

35 parts of the copper salt of NCH
25 parts of monoethanolamine
40 parts of H$_2$O.

EXAMPLE 13

Wood preservative consisting of:

35 parts of the nickel salt of NCH
15 parts of diethylenetriamine
50 parts of H$_2$O.

EXAMPLE 14

Wood preservative consisting of:

35 parts of the cobalt salt of NCH
16 parts of dipropylenetriamine
49 parts of H$_2$O.

EXAMPLE 15

Wood preservative consisting of:

35 parts of the copper salt of NCH
35 parts of tripropylenetetramine
35 parts of boric acid
45 parts of H$_2$O.

In the foregoing examples the heavy metal salts and the salts of NCH were used in approximately equivalent amounts; after impregnation the NCH, in the form of its heavy metal salts, was thus able to be almost completely fixed in the wood. However, a ratio may also be employed which ensures an excess of alkali metal or amine salts of NCH in the wood preservatives, thus enabling additional diffusible active ingredients to be retained in the wood after fixing.

The fungicides according to the invention penetrate the wood much more deeply than conventional fungicides containing an alkali metal hydroxide and a zinc salt of NCH (German Laid-Open Application DOS No. 1,817,579). This penetrating effect of the fungicides of the invention is of considerable importance in the case of wood which is difficult to impregnate, e.g., spruce, as it is thus possible to provide lasting protection against ligniperdous fungi.

EXAMPLE 16

Five 110 to 120 cm lengths of spruce (sapwood breadth: about 5 cm) are impregnated by vacuum pressure method with the fungicide solution of Example 12 which has been diluted to a content of 1 wt% of the copper salt of NCH (vacuum of 30 to 60 mm for 1 hour; impregnation for 2 hours at a pressure of 8 atmospheres gauge). Upon completion of impregnation, the copper salt of NCH is detectable over the whole sapwood breadth. For comparison, spruce was similarly treated with a prior art (2%) fungicidal solution prepared as follows.

67 parts (by weight) of $Al_2(SO_4)_3 \cdot 18H_2O$ is dissolved in 1,800 parts of water. 460 parts of 2N caustic solution is then added. While stirring, 50.8 parts of the 98% sodium salt of NCH is dissolved in this solution, and the whole made up to 2,500 parts with water.

After the detecting agent (5% iron chloride solution) had been sprayed onto slices cut from the samples, it was ascertained that the comparative agent had only penetrated the wood to a depth of from 0.5 to 1 cm.

We claim:

1. A fungicidal composition for wood preservation consisting essentially of the water-soluble complex compound of a heavy metal salt of N-nitroso-N-cyclohexylhydroxylamine, said heavy metal being selected from the group consisting of copper, zinc, cadmium, nickel and cobalt, and a complexing agent selected from the group consisting of ammonia and organic or inorganic compounds having at least one amine group capable of entering into a complex with said heavy metal to convert said heavy metal salt into a water-soluble complex salt.

2. A composition as claimed in claim 1 wherein said complexing agent is an alkylamine, dialkylamine, alkylenediamine or polyalkylene polyamine.

3. A composition as claimed in claim 1 wherein said complexing agent is monoethanolamine.

4. A composition as claimed in claim 1 added to water in a fungicidally effective proportion.

5. A composition as claimed in claim 1 added to water in a proportion of 0.1 to 10% by weight.

6. A process for protecting wood against fungus attack which comprises impregnating the wood to be protected with an aqueous solution containing a fungicidally effective amount of the water-soluble complex compound of a heavy metal salt of N-nitroso-N-cyclohexylhydroxylamine, said heavy metal being selected from the group consisting of copper, zinc, cadmium, nickel and cobalt, and a complexing agent selected from the group consisting of ammonia and organic or inorganic compounds having at least one amine group capable of entering into a complex with said heavy metal to convert said heavy metal salt into a water-soluble complex salt.

7. A process as claimed in claim 6 wherein said aqueous solution contains about 0.1 to 10% by weight of said water-soluble complex compound.

8. A process as claimed in claim 6 wherein said aqueous solution contains about 1 to 2% by weight of said water-soluble complex compound.

9. A process as claimed in claim 6 wherein said complexing agent is an alkylamine, dialkylamine, alkylenediamine or polyalkylene polyamine.

10. A process as claimed in claim 6 wherein said complexing agent is monoethanolamine.

* * * * *

UNITED STATES PATENT AND TRADEMARK OFFICE
CERTIFICATE OF CORRECTION

PATENT NO. : 4,143,153
DATED : March 6, 1979
INVENTOR(S) : Ernst-Heinrich Pommer et al It is certified that error appears in the above-identified patent and that said Letters Patent are hereby corrected as shown below:

Col. 5, line 20, "or" should be -- and --.

Col. 6, line 14, "or" should be --- and ---.

Signed and Sealed this

Sixteenth Day of October 1979

[SEAL]

Attest:

RUTH C. MASON
Attesting Officer

LUTRELLE F. PARKER
Acting Commissioner of Patents and Trademarks